(12) United States Patent
Ramaiah

(10) Patent No.: US 8,314,065 B2
(45) Date of Patent: Nov. 20, 2012

(54) METHOD OF REDUCTION OF WRINKLES ON SKIN OR ACCELERATION OF WOUND HEALING BY APPLYING PEPTIDES RELATED TO BASIC FIBROBLAST GROWTH FACTOR (BFGF)

(76) Inventor: Abburi Ramaiah, Calcutta (IN)

( * ) Notice: Subject to any disclaimer, the term of this patent is extended or adjusted under 35 U.S.C. 154(b) by 97 days.

(21) Appl. No.: 12/764,530

(22) Filed: Apr. 21, 2010

(65) Prior Publication Data

US 2010/0323962 A1    Dec. 23, 2010

Related U.S. Application Data

(62) Division of application No. 12/066,786, filed as application No. PCT/IN2006/000370 on Sep. 11, 2006, now abandoned.

(30) Foreign Application Priority Data

Sep. 13, 2005    (IN) .............................. 847/KOL/2005

(51) Int. Cl.
   *A61K 38/08*    (2006.01)
   *A61K 38/10*    (2006.01)
   *A61K 38/12*    (2006.01)
   *A61K 38/18*    (2006.01)
   *C07K 7/00*     (2006.01)
   *C07K 7/64*     (2006.01)
   *C07K 14/50*    (2006.01)

(52) U.S. Cl. ...... 514/9.1; 514/18.6; 514/18.8; 514/21.4; 514/21.5; 514/21.6

(58) Field of Classification Search .............. None
See application file for complete search history.

(56) References Cited

U.S. PATENT DOCUMENTS

| | | | |
|---|---|---|---|
| 5,252,718 A | | 10/1993 | Baird et al. |
| 5,492,894 A | | 2/1996 | Bascom et al. |
| 6,143,723 A | * | 11/2000 | Ramaiah ................... 514/9.1 |

FOREIGN PATENT DOCUMENTS

| | | |
|---|---|---|
| AU | 199723507 B2 | 11/1997 |
| EP | 0505108 A1 | 9/1992 |
| EP | 0894493 A1 | 2/1999 |
| IN | 185703 | 5/1996 |
| IN | 186437 | 9/2010 |
| JP | 543442 A | 2/1993 |

OTHER PUBLICATIONS

Griffiths et al., Restoration of collagen formation in photodamaged human skin by tretinoin (retinoic acid). New Eng. J Med (1993); 329:530-535.

Baird et al., Receptor- and heparin-binding domains of basic fibroblast growth factor. Proc Natl Acad Sci (1988); 85 (7) 2324-2328.

Brincat et al., Sex hormones and skin collagen content in postmenopausal women. Br Med. J (1983); 287: 1337-1338.

\* cited by examiner

*Primary Examiner* — Christine J Saoud
(74) *Attorney, Agent, or Firm* — The Webb Law Firm

(57) ABSTRACT

The present invention is directed to synergistic therapies for the treatment of vitiligo. Particularly, the invention is directed to a composition for the reduction of wrinkles on skin, the acceleration of wound healing, and the darkening of hair including a peptide and an acceptable carrier. The peptide may be selected from the group consisting of the peptide of SEQ. ID 1, the peptide of SEQ. ID 2, the peptide of SEQ. ID 3, the peptide of SEQ. ID 4, the peptide of SEQ. ID 5, the peptide of SEQ. ID 6, the peptide of SEQ. ID 7, and the peptide of SEQ. ID 8.

3 Claims, 5 Drawing Sheets

Before

After

Treated (After application for 6 weeks)

Controlled

FIG. 2B Control
(Formulation only applied for 6 weeks)

| SEQ. ID NO: 1 ||
|---|---|
| Sequence Characteristics ||
| Length | 10 amino acids |
| Type | Amino acid |
| Strandedness | N/A |
| Topology | Linear |
| Source | Synthetic, non-bacterial source |
| Molecular Type | Peptide |
| Sequence Description | Described starting from the amino terminus of the peptide: the standard 3-letter description of the amino acid is used |
| | Tyr Arg Ser Arg Lys Tyr Ser Ser Trp Tyr amide |
| SEQ. ID NO: 2 ||
| Sequence Characteristics ||
| Length | 10 amino acids |
| Type | Amino acid |
| Strandedness | N/A |
| Topology | Linear |
| Source | Synthetic, non-bacterial source |
| Molecular Type | Peptide |
| Sequence Description | Described starting from the amino terminus of the peptide: the standard 3-letter description of the amino acid is used |
| | Tyr Arg Ser Arg Lys Tyr Glu Ser Trp Tyr amide |
| SEQ. ID NO: 3 ||
| Sequence Characteristics ||
| Length | 10 amino acids |
| Type | Amino acid |
| Strandedness | N/A |
| Topology | Cyclic |
| Source | Synthetic, non-bacterial source |
| Molecular Type | Peptide |
| Sequence Description | Described starting from the amino terminus of the peptide: the standard 3-letter description of the amino acid is used |
| | Cyclo(Tyr Arg Ser Arg Lys Tyr Glu Ser Trp Tyr) |
| SEQ. ID NO: 4 ||
| Sequence Characteristics ||
| Length | 11 amino acids |
| Type | Amino acid |
| Strandedness | N/A |
| Topology | Cyclic |
| Source | Synthetic, non-bacterial source |
| Molecular Type | Peptide |
| Sequence Description | Described starting from the amino terminus of the peptide: the standard 3-letter description of the amino acid is used |
| | Cyclo(Gly Tyr Arg Ser Arg Lys Tyr Ser Ser Arg Tyr) |

FIG. 4A

| SEQ. ID NO: 5 | |
|---|---|
| Sequence Characteristics | |
| Length | 15 amino acids |
| Type | Amino acid |
| Strandedness | N/A |
| Topology | Linear |
| Source | Synthetic, non-bacterial source |
| Molecular Type | Peptide |
| Sequence Description | Described starting from the amino terminus of the peptide: the standard 3-letter description of the amino acid is used |
| | Tyr Arg Ser Arg Lys Tyr Ser Ser Trp Tyr Val Ala Leu Lys Arg |
| SEQ. ID NO: 6 | |
| Sequence Characteristics | |
| Length | 24 amino acids |
| Type | Amino acid |
| Strandedness | N/A |
| Topology | Linear |
| Source | Synthetic, non-bacterial source |
| Molecular Type | Peptide |
| Sequence Description | Described starting from the amino terminus of the peptide: the standard 3-letter description of the amino acid is used |
| | Pr Ala Leu Pro Glu Asp Gly Gly Ser Gly Ala Phe Pro Pro Gly His Phe Lys Asp Pro Lys Arg Leu Tyr |
| SEQ. ID NO: 7 | |
| Sequence Characteristics | |
| Length | 10 amino acid residues |
| Type | Amino acid |
| Strandedness | N/A |
| Topology | Linear |
| Source | Synthetic, non-bacterial source |
| Molecular Type | Peptide |
| Sequence Description | Described starting from the amino terminus of the peptide: the standard 3-letter description of the amino acid is used |
| | Para hydroxyl phenyl propionic-amide-Tyr Arg Ser Arg Lys Tyr Ser Ser Trp Tyr amide |

FIG. 4B

| Sequence ID 8 | |
|---|---|
| Sequence Characteristics | |
| Length | 10 amino acids |
| Type | Amino acid |
| Strandedness | N/A |
| Topology | Linear |
| Source | Synthetic, non-bacterial source |
| Molecular Type | Peptide |
| Sequence Description | Described starting from the amino terminus of the peptide: the standard 3-letter description of the amino acid is used |
| | Tyr Arg Ser Arg Lys Tyr Ser Ser Trp Tyr-NH(CH$_2$)$_2$C$_6$H$_4$OHp |
| | |
| | |
| | |

FIG. 4C

SEQUENCE LISTING

```
<160> NUMBER OF SEQ ID NOS: 8

<210> SEQ ID NO 1
<211> LENGTH: 10
<212> TYPE: PRT
<213> ORGANISM: Artificial Sequence
<220> FEATURE:
<221> NAME/KEY: AMIDE
<222> LOCATION: (1)  (10)
<223> OTHER INFORMATION: Synthetic. The C terminus is an Amide.

<400> SEQUENCE: 1

Tyr Arg Ser Arg Lys Tyr Ser Ser Trp Tyr
1               5                   10

<210> SEQ ID NO 2
<211> LENGTH: 10
<212> TYPE: PRT
<213> ORGANISM: Artificial Sequence
<220> FEATURE:
<221> NAME/KEY: AMIDE
<222> LOCATION: (1)  (10)
<223> OTHER INFORMATION: Synthetic. The C terminus is an Amide.

<400> SEQUENCE: 2

Tyr Arg Ser Arg Lys Tyr Glu Ser Trp Tyr
1               5                   10

<210> SEQ ID NO 3
<211> LENGTH: 10
<212> TYPE: PRT
<213> ORGANISM: Artificial Sequence
<220> FEATURE:
<221> NAME/KEY: CYCLIC PEPTIDE
<222> LOCATION: (1)  (10)
<223> OTHER INFORMATION: Synthetic. The peptide is Cyclic Peptide.

<400> SEQUENCE: 3

Tyr Arg Ser Arg Lys Tyr Ser Ser Trp Tyr
1               5                   10

<210> SEQ ID NO 4
<211> LENGTH: 11
<212> TYPE: PRT
<213> ORGANISM: Artificial Sequence
<220> FEATURE:
<221> NAME/KEY: CYCLIC PEPTIDE
<222> LOCATION: (1)  (11)
<223> OTHER INFORMATION: Synthetic.  This is a Cyclic Peptide.

<400> SEQUENCE: 4

Gly Tyr Arg Ser Arg Lys Tyr Ser Ser Trp Tyr
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Tyr Arg Ser Arg Lys Tyr Ser Ser Trp Tyr Val Ala Leu Lys Arg
1               5                   10                  15

<210> SEQ ID NO 6
<211> LENGTH: 24
<212> TYPE: PRT
<213> ORGANISM: Artificial Sequence
<220> FEATURE:
```

-continued

```
<223> OTHER INFORMATION: Synthetic

<400> SEQUENCE: 6

Pro Ala Leu Pro Glu Asp Gly Gly Ser Gly Ala Phe Pro Pro Gly His
1               5                   10                  15

Phe Lys Asp Pro Lys Arg Leu Tyr
            20

<210> SEQ ID NO 7
<211> LENGTH: 10
<212> TYPE: PRT
<213> ORGANISM: Artificial Sequence
<220> FEATURE:
<221> NAME/KEY: N and C terminus Modification
<222> LOCATION: (1)   (10)
<223> OTHER INFORMATION: The N terminus is coupled to Para Hydroxy
      Phenyl proprionic acid/Myrestic acid or/ any other Lipophilic
      acid. The C terminus is an Amide. Synthetic.

<400> SEQUENCE: 7

Tyr Arg Ser Arg Lys Tyr Ser Ser Trp Tyr
1               5                   10

<210> SEQ ID NO 8
<211> LENGTH: 10
<212> TYPE: PRT
<213> ORGANISM: Artificial Sequence
<220> FEATURE:
<221> NAME/KEY: The C terminus Modification
<222> LOCATION: (1)   (10)
<223> OTHER INFORMATION: The C terminus is coupled to Parahydroxy
      Phenylpropionic acid or any Lipophilic moiety. Synthetic.

<400> SEQUENCE: 8

Tyr Arg Ser Arg Lys Tyr Ser Ser Trp Tyr
1               5                   10
```

METHOD OF REDUCTION OF WRINKLES ON SKIN OR ACCELERATION OF WOUND HEALING BY APPLYING PEPTIDES RELATED TO BASIC FIBROBLAST GROWTH FACTOR (BFGF)

CROSS-REFERENCE TO RELATED APPLICATIONS

This application is a divisional application of U.S. patent application Ser. No. 12/066,786, filed on Jul. 30, 2008, which is a national stage filing under 35 U.S.C. §371 of PCT/IN2006/000370, filed Sep. 11, 2006, and of Indian Patent Application No. 847/KOL/2005, filed Sep. 13, 2005. The entire contents of the above-referenced applications are incorporated herein by reference.

BACKGROUND OF THE INVENTION

1. Field of Invention

This invention relates to agonist peptides of basic fibroblast growth factor (bFGF) and the method of reduction of wrinkles on skin, darkening of hair and acceleration of wound healing.

2. Description of Related Art

Basic fibroblast growth factor (bFGF) also known as FGF2, so named because it contains a high number of basic amino acid residues (Lysin, Arginie and Histidine) is a potent mitogen for a variety of cell types including melanocytes, keratinocytes, and the major cell type in the epidermal unit and fibroblasts located in the dermis of skin. Both bovine and human bFGF were isolated and the genes expressing this product were sequenced and cloned. In addition, bFGF was found to be expressed in a wide variety of tissue types including placenta, keratinocytes, and fibroblasts.

We have earlier described that bFGF may be involved in repigmentation of vitiligo macules, a pigmentary disorder characterized by patchy depigmentation of skin (Ramaiah, A; Puri, N; and Majamdar, M. A new hypothesis for etiology of vitiligo in Acte Derma Venereol (Stockholm), 1989, 69:323-327). This idea was tested first on the in-vitro melanocyte cell cultures from the uninvolved areas of untreated vitiligo subjects and later on mixed cell cultures of melanocytes and keratinocytes obtained from the uninvolved areas of untreated vitiligo subjects. The results demonstrated that bFGF corrects all the abnormalities of melanocytes obtained from the uninvolved areas of untreated vitiligo subjects. An animal model was developed to resemble vitiligo to test the efficacy of interdermal injection bFGF on the rate of repigmentation of depigmented ear lobes of Guinea pigs and depigmented ear lobes of Guinea pigs and depigmented skin patches of Yucatan swine. They were found effective. Peptides ranging from deca peptide to 24 amino acid long peptide were tested for the efficacy to repigment the depigmented ear lobes of Guinea pigs and the depigmented skin patches of Yucatan swine. These peptides were shown to be specific since other growth factors like epidermal growth factor or peptide 1-12 of bFGF did not have any effect on the repigmenting of depigmented patches on the experimental animals.

Patents of interest describing bFGF or peptides described above and the formulation for their penetration through intact skin include U.S. Pat. No. 6,143,723; AU Patent No. 722626; Indian Patent Nos. 185613, 186437, and 185703.

The peptides were tested on human volunteers suffering from vitiligo in the various phases of clinical trials in India and found to be successful in repigmenting about more than 80% of the volunteers with stable generalized vitiligo and segmental vitiligo.

Skin is subject to aging and is visible to the naked eye. The aging process of skin can be divided into chrono aging and photo aging. The former is a normal aging process and can be accelerated by the exposure of skin to sun, which is known as photo aging. In addition, skin is subject to deterioration through dermatological disorders, and environmental abuse.

Exposure of white, very fair skin to ultraviolet radiation results in more wrinkling of skin than the more pigmented skin. Skin wrinkles are a reminder to the individual that he/she is looking older and, therefore, individuals like to reduce skin wrinkles by application to the skin of various cosmetic creams and/or moisturizers. Failing that, the use of various forms of cosmetic surgery which treat or delay the visible signs of chrono aging/photo aging such as wrinkles, lines, sagging etc. can be attempted.

There is a vast amount of epidemiological literature relating to thinning of skin to aging. Collagen-1 represents more than 70% of the dermis of the skin. (Uitto J. Connective tissue biochemistry of the aging dermis: Age related alterations in collagen and elastin: Dermatio. Clin (1986) 4:433-46). Dermal collagen content peaks in the third decade of life and declines gradually at a rate approximately 1% per year thereafter in men and women (Artho P. Skin thickness and collagen content in some endocrine, connective tissue and skin diseases. Acta derm. Veneroeol Suppl (Stockh) 1972: 69:1-48. Meema H E, Sheppard R H, Roentgen graphic visualization and measurement of skin thickness and its diagnostic application to acromegaly, Radiology (1964); 82:411-7, Shuster S, Black M M, Mc Vitie E:. The influence of age and sex on skin thickness, skin collagen and density Br J Dermatol (1975); 93:639-43, Shuster S Bottoms E senile feneration of skin collagen in men. In women it may be so after the fifth decade of life.

Collagen is the predominant matrix skin protein and is known to impart tensile strength to skin. Decorin is proteoglycan, which is known to be important for controlled and correct deposition of collagen in the extracellular matrix of skin. It is also known in the art that the levels of collagen and decorin in skin are significantly reduced with age and/or photo damaged skin. Many studies had shown that the levels of collagen type 1 in skin are decreased with age and/or with increased photo damage (Lavaker R, Jour. Invest. Dermatol (1979); 73:59-66 Griffiths et al New. Eng J. med (1993); 329, 5300535). In the case of decorin, it has been shown that mRNA expression of the proteoglycan is greatly reduced in photo-damaged skin in vitro (Bernstein et al. Lab Invest (1995); 72:662-669). The reduction of the levels of these skin proteins is accordingly associated with collagen, elastin also is lost with age. So the skin gets thinner with age and has a tougher time getting enough moisture to the epidermis. At about the same time the fat in the subcutaneous layer (which gives skin a plump firm appearance) also begins to disappear. The epidermis begins to sag, and wrinkles form. Wrinkles are then prone in the face where facial muscle contractions have been repeated over many years.

In addition to gradually aging and sun exposure there are a number of other factors that can contribute increased wrinkles. Some of these can be controlled, while others cannot. The most common factors that determine wrinkle occurrence include the following:
 Heredity
 Skin type
 Smoking
 Hair style Sun exposure Drug use Wrinkles on the face are due to repeated nerve stimulation that results in repeated facial muscle contractions, in addition to reduction in the amount of collagen, elastin and subcutaneous fat in the skin. All anti-wrinkling agents which reduce the nerve stimulation and, thus, facial muscle contractions, can help in the reduction of fine lines and wrinkles on the face.

Wrinkle reduction on the rest of the skin on the body, including the skin on the face, should essentially be by increasing the synthesis of collagen retention in the skin of moisture.

It is well known in the art that retinoic acid is a potent anti-aging agent and induces dermal repair of photo damaged skin. It was shown that wrinkle effacement and dermal repair following topical treatment of skin with retinoic acid arises through new collagen deposition and synthesis in skin (Griffiths et al New, Eng. J, Med (1993); 329, 530-535).

SUMMARY OF THE INVENTION

An object of the present invention is to propose a peptide and composition containing said peptide for reducing the formation of wrinkles on skin.

Another object of this invention is to propose a peptide and a composition containing said peptide, for darkening of hair.

BRIEF DESCRIPTION OF THE DRAWINGS

FIG. 2B shows a right dorsal hand of a volunteer treated only by placebo;

FIG. 4 is a table of SEQ ID NOs: 1-8.

BRIEF DESCRIPTION OF THE INVENTION

According to this invention there is provided the peptides consisting of SEO ID NOs: 1-8 listed herein for darkening and reducing formation of wrinldes on skin. The peptides are present in the range 0.02-5% w/w in the composition are effective when applied topically in the formulation for reduction of wrinkles on skin, and in darkening of hair. They can be applied in the form of lotion, gels or creams. The mode of administration is not restricted to the above methods.

EXAMPLE 1

Anti-Wrinkle

Figure 1A:
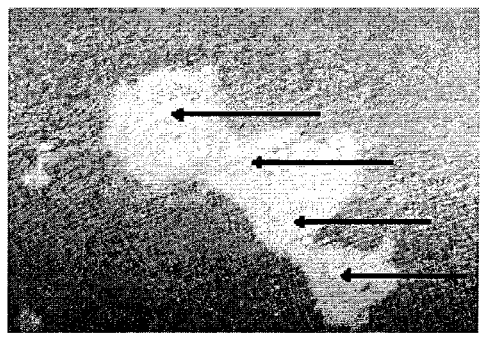
FIG. 1A shows skin before topical application of the composition.
Figure 1B:
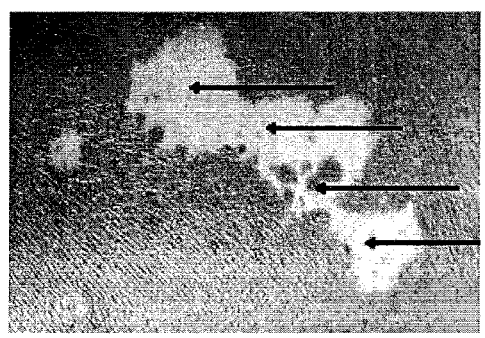
FIG. 1B shows skin after topical application of the composition.

Based on the observations presented in FIGS. 1*a* and 1*b*, a planned clinical trial was conducted on 20 normal volunteers with clear skin who were chosen for this clinical trial. The application of either placebo (formulation) on the right dorsal part of the hand or the formulation containing the peptide was topically applied on the left dorsal hand of the volunteer once a day for 6 weeks and the pictures were taken at the end of such trial.

Figure 2A:
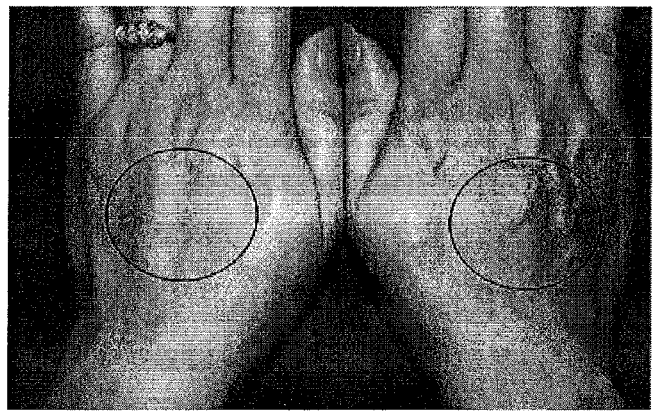
FIG. 2A shows a left-dorsal hand of a volunteer after application of the composition for six weeks.

The results indicated that topical application of the peptide in the formulation once a day for 6 weeks results without exception in a reduction in wrinkles. A representative photograph after 6 weeks of application of the peptide in the formulation on dorsal hands reduced wrinkles, as compared to the control where only the formulation was topically applied. On stopping of the topical application of the peptide lotion, the skin returns to normal in about 2-2 and half months. This effect is thus not permanent. The reduction of wrinkles on skin by the topical application of the bFGF derived peptide described above may be due to increased cellularity of the epidermis and also increased synthesis of collagen. FIG. 2 shows the reduction of wrinkles on left dorsal hand of a volunteer after application of the composition with the peptide for 6 weeks as compared to the dorsal right hand only with placebo.

EXAMPLE 2

Drawing of Hair

Figure 3:
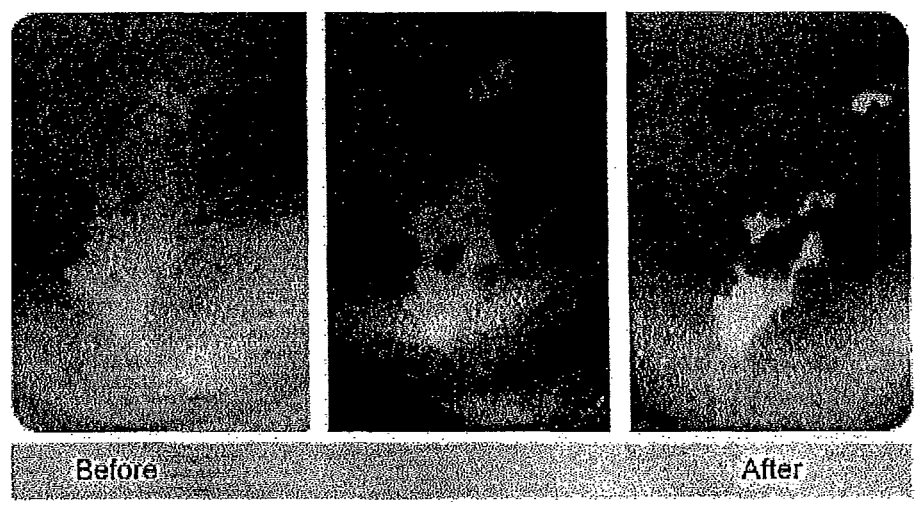
FIG. 3 shows hair follicles before treatment with the composition and after treatment with the composition for 3-6 months.

In addition, during the clinical trial of its use for the treatment of vitiligo it was observed that the peptides were able to repigment white hair located in the vitiligo macules. Therefore, these peptides increase the proliferation of melanocytes located not only in the dermal epidermal junction, but also the melanocytes located in the hair follicles, as indicated in the photographs (FIG. 3), taken before and after the topical application of these peptides for 3-6 months.

Peptides Derived from bFGF may Accelerate Wound Healing

Advanced wound care technologies have emerged from the shadow to become, in the last 20 years, significant products in wound treatment. While conventionally made wound care products are considerable and generally less expensive, new products and biotechnological advancements are beginning to revolutionize the wound care market. New technological products are competing in a fast track market that seeks to improve the quality of life for millions of individuals needing both acute and chronic wound care.

The subcutaneous implantation of poly-vinyl alcohol sponges had been used to generate artificial wound space. Healing process was followed with time by a combination of histological and biochemical analyze of new tissue that grows in to the interstices of the sponge material in presence and absence of recombinant basic fibroblast growth factor. The results of these experiments clearly indicated that recombinant basic fibroblast growth factor acts to increase neo vascularisation the number of fibroblasts and the deposition of collagen in the wound space. Similar results were seen on wounds of diabetic mice. There were no side effects (Bernstein et al Lab. Invest. 14995); 72: 662-669).

In view of the fact that the peptides listed herein are agonist peptides of bFGF, it is indeed possible that these peptides may accelerate wound healing as the bFGF does by topical application of an effective amount of any of the peptides listed in a composition in sterile phosphate buffered isotonic saline solution.

The invention claimed is:

1. A method of reducing wrinkles on skin or accelerating wound healing in a patient in need thereof comprising:
administering to a subject a composition comprising an agonist peptide of bFGF selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8.

2. The method of reducing wrinkles on skin or accelerating wound healing in a patient in need thereof of claim 1, wherein said composition further comprises an acceptable carrier for said peptide.

3. The method of reducing wrinkles on skin or accelerating wound healing in a patient in need thereof of claim 2, wherein said composition is administered topically.

* * * * *